United States Patent [19]
Grundy et al.

[11] Patent Number: 5,603,697
[45] Date of Patent: Feb. 18, 1997

[54] STEERING MECHANISM FOR CATHETERS AND METHODS FOR MAKING SAME

[75] Inventors: David A. Grundy, Fremont, Calif.;
Brian M. Packard, Monticello, Minn.;
Glen G. Warner, Morgan Hill, Calif.

[73] Assignee: Fidus Medical Technology Corporation, Fremont, Calif.

[21] Appl. No.: 388,373

[22] Filed: Feb. 14, 1995

[51] Int. Cl.⁶ ................................................ A61M 37/00
[52] U.S. Cl. ........................... 604/95; 607/101; 607/156
[58] Field of Search ................ 604/95, 114, 105; 606/41, 33, 34, 42; 607/101, 156, 154, 98, 99, 122, 123; 600/114, 139, 146

[56] References Cited

U.S. PATENT DOCUMENTS

| | | | |
|---|---|---|---|
| 5,364,352 | 11/1994 | Cimino et al. | 604/95 |
| 5,370,644 | 12/1994 | Langberg | 607/122 X |
| 5,391,147 | 2/1995 | Imran et al. | 604/95 |
| 5,397,304 | 3/1995 | Truckai | 604/95 |
| 5,405,346 | 4/1995 | Grundy et al. | 606/41 |
| 5,487,757 | 1/1996 | Truckai et al. | 604/95 X |

*Primary Examiner*—Corrine M. McDermott
*Assistant Examiner*—N. Kent Gring
*Attorney, Agent, or Firm*—Hickman Beyer & Weaver

[57] ABSTRACT

A medical catheter steering construction is described that is particularly well suited for steering ablation catheters that utilize coaxial transmission lines. An elongated coaxial transmission line is received within a lumen in the flexible tubular member. An antenna is coupled to the center conductor of the coaxial transmission line. A shield termination is secured to the shield portion of the coaxial transmission line. A steering wire that extends through the tubular member to permit a user to steer the catheter during insertion is attached to the shield termination. With this arrangement, when the catheter is inserted into the vessel of a patient, the tip of the catheter may be steered by pulling on the steering wire. In one embodiment of the invention, a distal portion of the tubular member has a stiffness that is significantly less than the stiffness of the majority of the tubular member to facilitate bending during steering. Suitable methods for making such catheters are also described.

16 Claims, 9 Drawing Sheets

STEERING MECHANISM FOR CATHETERS AND METHODS FOR MAKING SAME

This application relates generally to co-pending application Ser. No. 08/300,948 filed Sep. 6, 1994, which is incorporated herein by reference.

BACKGROUND OF THE INVENTION

The present invention relates generally to a steering mechanism for catheter systems. The described steering mechanism is particularly well suited for use in catheter systems that use electromagnetic energy transmitted over a coaxial transmission line to ablate internal bodily materials.

Catheter ablation has recently become an important therapy for certain cardiac arrhythmias. Radio frequency (RF) energy is presently accepted as the preferred ablating energy source. Accordingly, a variety of RF catheters and power supplies are currently available to electrophysiologists. Radio frequency energy has several limitations including the rapid dissipation of energy in surface tissues resulting in shallow "burns" and failure to access deeper arrhythmogenic tissues. Another limitation is the risk of clot formation on the energy emitting electrodes. Such clots have an associated danger of causing potentially lethal strokes in the event that a clot is dislodged from the catheter. For these and other reasons, significant attention has been given recently to alternative ablative energy sources.

Microwave frequency energy has long been recognized as an effective energy source for heating of biological tissues and has seen use in such hyperthermia applications as cancer treatment and preheating of blood prior to infusions. Accordingly, in view of the drawbacks of the traditional catheter ablation techniques, there has recently been an interest in using microwave energy as an ablation energy source. The advantage of microwave energy is that it is much easier to control and safer than direct current applications and it is capable of generating substantially larger lesions than RF catheters, which greatly simplifies the actual ablation procedures.

In U.S. Pat. No. 4,641,649, Walinsky et al. disclose a medical procedure for the treatment of tachycardia and cardiac disrhythmia which uses microwave frequency electro magnetic energy to ablate selected cardiac tissue. The microwave energy is transmitted over a coaxial transmission line having an antenna at its distal end. A similar procedure is disclosed in Langberg et al's article entitled "Catheter Ablation of the Atrioventricular Junction Using a Helical Microwave Antenna: A Novel Means of Coupling Energy to the Endocardium," *PACE*, pp. 2105–2113 Vol. 14 (1991). As suggested in the title, the Langberg et al. article proposes the use of a helical microwave antenna at the distal end of the catheter in order to improve the catheter's power delivery characteristics. Other similar devices are disclosed in Langberg's U.S. Pat. Nos. 4,945,912 and 5,246,438. In all microwave ablation devices it is desirable to develop and maintain a sharp and predictable electromagnetic field.

Another requirement of most catheters is that some type of steering mechanism must be provided to permit the cardiologist to direct the antenna portion of the catheter to the proper location. Although a wide variety of steering mechanisms are currently in use, there are continuing efforts to provide improved steering systems.

SUMMARY OF THE INVENTION

To achieve the foregoing and other objects and in accordance with the purpose of the present invention, a medical catheter steering construction is described that is particularly well suited for steering ablation catheters that utilize coaxial transmission lines. In one embodiment, the catheter is formed from a flexible tubular member adapted to be inserted into a vessel in the body of a patient. An elongated coaxial transmission line is and received within a lumen in the flexible tubular member. The coaxial transmission line includes a center conductor, a shield and a dielectric that electrically insulates the center conductor from the shield. An antenna is coupled to the center conductor of the coaxial transmission line. A shield termination is secured to the shield portion of the coaxial transmission line. A steering wire that extends through a tube encapsulated in the flexible tubular member is attached to the shield termination. With this arrangement, when the catheter is inserted into the vessel of a patient, the tip of the catheter may be steered by pulling on the steering wire.

In another embodiment of the invention, a distal portion of the tubular member has a stiffness that is significantly less than the stiffness of the majority of the tubular member to facilitate bending during steering. The geometry of the shield termination may be varied greatly. In one preferred embodiment, it constitutes an annular member that permits the coaxial transmission line to pass there through.

Suitable methods for making such catheters are also described. In one embodiment, an elongated flexible tubular member that is sized suitably to be inserted into a vessel in the body of a patient is formed such that a first portion of the tubular member has a stiffness that is significantly less than the stiffness of the majority of the tubular member. A shield termination ring is secured to the distal end of a braided shield portion of the coaxial transmission line. One or more steering wires are then attached to the shield termination ring. The coaxial transmission line and the steering wires assembly is then inserted into the flexible tubular member as a unit. Thereafter a cap is secured to the distal end of the flexible tubular member to enclose the antenna.

In one embodiment, the first portion of the tubular member is formed from a material having a first stiffness and the second portion (majority) of the tubular member is separately formed from a stiffer material. The first and second portions of the tubular member are then heated to a glass point and bonded together at that state.

BRIEF DESCRIPTION OF THE DRAWINGS

The invention, together with further objects and advantages thereof, may best be understood by reference to the following description taken in conjunction with the accompanying drawings in which:

FIG. 7 is a diagrammatic cross sectional view illustrating a single-lumen flexible member and the components that pass there through.

DETAILED DESCRIPTION OF THE INVENTION

The present invention relates generally to medical catheter systems. To facilitate description of the present invention, its application in a microwave ablation catheter system that uses a coaxial transmission line to transmit electromagnetic energy to an antenna mounted at the distal end of the catheter will be described. As is well known to those skilled in the art, medical catheter systems typically include an elongated catheter having a working member disposed near the distal tip of the catheter and a transmission line for actuating and/or powering the working member. The transmission line passes through an elongated tubular member. A handle is typically positioned near the proximal end of the catheter to permit the user (typically a doctor) to control the catheter. Additionally, a connector is typically provided at the proximal end of the catheter to facilitate connection to a base unit that powers the working member. In the described embodiment, the working member is the antenna, the base includes a microwave power supply and the transmission line is a coaxial cable. Although the invention will be described in conjunction with a microwave ablation catheter system, portions of the described invention may be used in other catheter systems as well.

Figure 1:
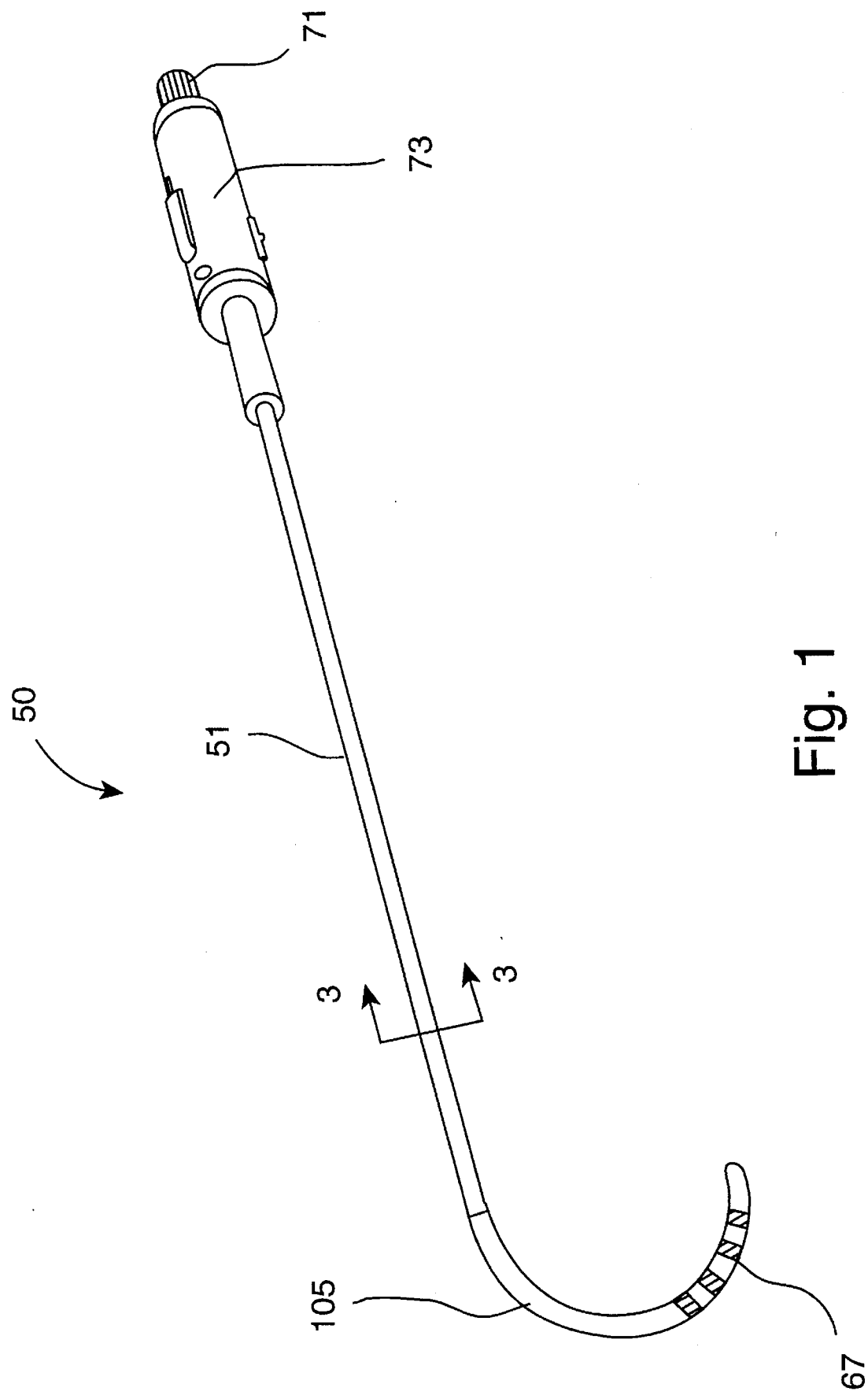
FIG. 1 is a diagrammatic view of an ablation catheter formed in accordance with one embodiment of the present invention.
Figure 3:
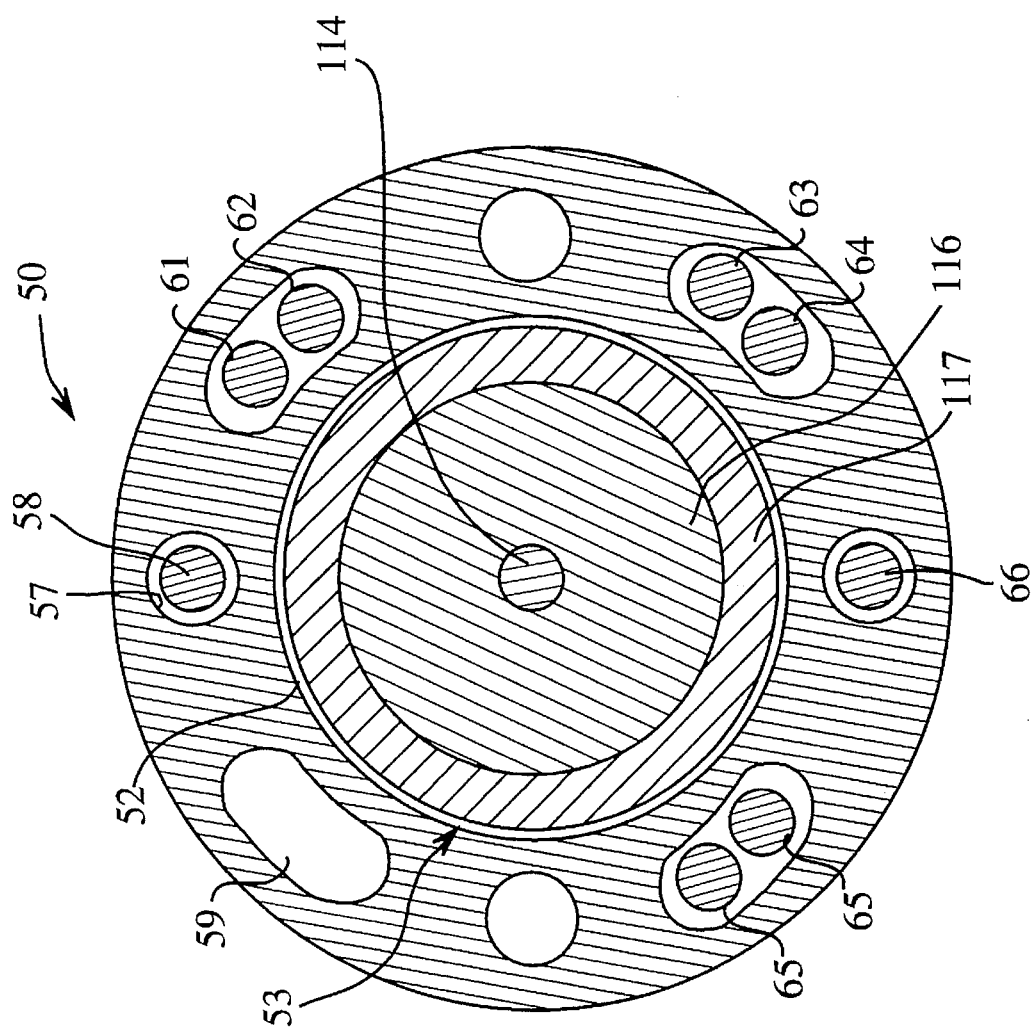
FIG. 3 is a diagrammatic cross sectional view of the ablation catheter illustrated in FIG. 1 taken along line 3—3 illustrating the multi-lumen flexible member and the components that pass through the various lumens.

Referring initially to FIGS. 1 and 3, a suitable catheter for incorporating the present invention will be described. The catheter 50 includes outer tubing 51, a coaxial microwave transmission line 53, a helical antenna 56, at least one stiffening wire 58, at least one steering wire 66, a plurality of electrode wires 61–64, thermometry elements 65, electrodes 67 and a connector 71. The outer tubing 51 may be made of any suitable material such as medical grade polyolefins, polyether, polyimides, fluoropolymers, or polyvinylidene fluoride. Further, PEBAX resins from Autochem of Germany have been used with success for the outer tubing of the body of the catheter. However, Teflon type products are preferred for the tip. The connector 71 couples the transmission line 53 to an external power supply.

The current thinking is that in order to transmit microwave energy in small diameter environments, the wave guide should be a coaxial cable. Therefore, a coaxial wave guide is selected that is suitable for transmitting microwave energy. A suitable wave guide is the CW4050-3050P coaxial cable supplied by Cooner of Chatsworth (Calif). Of course, the diameter of the coaxial transmission line 53 will vary depending upon the needs of a particular system. However, generally, the larger the diameter, the better the microwave transmission characteristics will be. By way of example, as indicated above, in coronary applications, the catheter diameter is typically limited to approximately 7½ French (approximately 2.5 mm in diameter). In such a system, a wave guide that is approximately one meter long and has a diameter of 72 thousandths of an inch (1.8 mm) works well. A metal collar is affixed to the distal end of the braided shield of the coaxial transmission line is used as a shield termination 130. The metal ring is also used to anchor steering wires 66 which may be used to bend the tip of the catheter to facilitate steering.

An antenna 56 is provided at the distal end of the transmission line. Although the geometry of the antenna may vary in accordance with the needs of a particular application, a helical coil type antenna having a total length (i.e. length of the wire along the coil as opposed to the longitudinal length of the coil) equal to either one eighth or one quarter of the wavelength of the transmitted microwave energy (or a multiple thereof) has been found to work particularly well when the goal is to develop a strong field to the side of the antenna, which is desirable for certain applications. This antenna configuration also exhibits particularly good coupling to the transmission line. In view of this characteristic, the optimal actual length of such an antenna will vary in accordance with the selected frequency. The characteristics of the helical coil type antenna are the result of a variety of characteristics including shield (ground plane) to antenna gap, coil pitch, wire size, wire geometry and coil diameter. In some embodiments, it may be desirable to fabricate an antenna having a rectangular cross section in order to improve the coil density. It should be appreciated that the actual antenna geometry can be varied widely in accordance with the type of ablation that is desired for a particular application. For example, the helical antenna shown is particularly good at developing a strong electromagnetic field to the side of the catheter tip. On the other hand, a straight antenna tip that extends slightly beyond a shield may be more effective at developing fields that extend from the distal end of the catheter.

A series of electrodes 67 may be provided near the tip of the catheter to monitor the patient's condition and/or the nature of the ablation process. In the described embodiment, the information obtained from the electrodes 67 is transmitted through the power supply to external electronics. Filtering of the signal may be provided as necessary. In alternative embodiments, some of the external electronics could be incorporated into the power supply and/or the power supply could use information obtained from the electrodes in its control scheme.

The thermometry elements 65 may take the form of thermocouple wires, fiber optic sensor cables or any other suitable thermometry devices. The catheter tip 100 is encased within an insulating shell 102 formed from a material with a low dielectric constant such as silicone or Teflon. The shell 102 insulates the antenna 56 to avoid the charring and tissue destruction effects that are commonly experienced with exposed (uninsulated) catheter tips. Details of suitable antennas and suitable catheter tip constructions are described in the related application referenced above.

Figure 2:
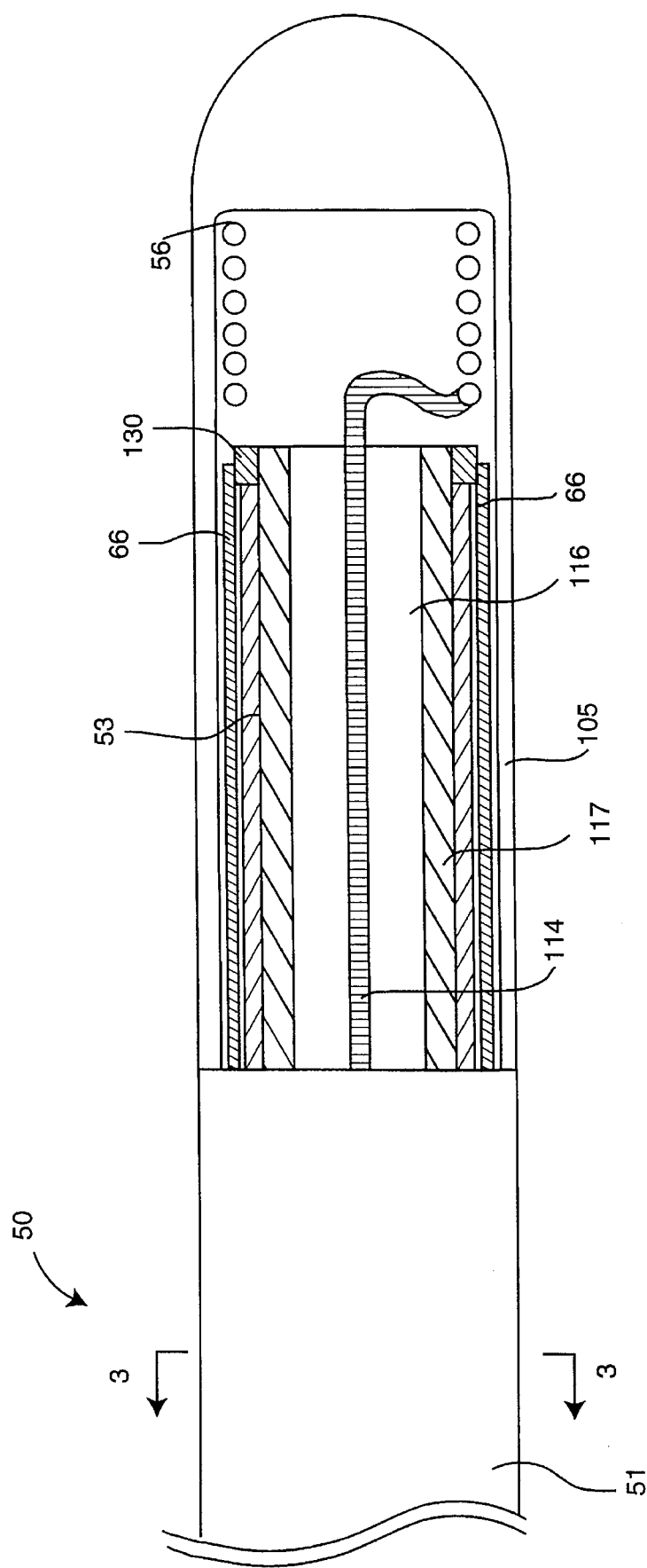
FIG. 2 is a diagrammatic partial cross sectional side view of the end portion of the ablation catheter illustrated in FIG. 1.

Referring next to FIG. 2, a presently preferred embodiment of the invention that includes a metal ring 130 that acts as both a shield termination and an anchor for the steering wires will be described. As indicated above, the outer tubing 51 is formed from a suitable medical grade material. By way of example PEBAX resin works well. The majority of the catheter is formed from a relatively stiff resin mixture. By way of example, durometer readings in the range of 30–70 shore D hardness work well. In one specific embodiment, material having durometer stiffness of 62 shore D hardness has been found to work well. An end portion 105 of the outer tubing 51 is formed such that its stiffness is less than that of the main portion of the outer tubing. The softer end portion 105 is the portion of the catheter that will bend during steering. By way of example, durometer readings in the range of 30 to 55 shore D hardness, as for example 45, have been found to work well to provide enough stiffness so that the catheter may be inserted into coronary vessels, yet flexible enough to follow the tortuous path required in order to position the catheter in the heart for treatment of tachycardia and cardiac disrhythmia. The actual length of the end portion 105 may vary in accordance with the requirements of a particular catheter. However, generally lengths in the range of two to eight centimeters has been found to work well for cardiac applications.

The coaxial transmission line 53 includes a center conductor 114, a dielectric support portion 116 that surrounds and insulates the center conductor and a braided shield portion 117. The shield 117 terminates proximally of the antenna. The center conductor is connected directly to the antenna. The dielectric support portion 116 of the coaxial transmission line may extend beyond the point where the braided shield is attached to the shield termination so that it extends coaxially through the entire antenna coil and into a supporting recess in a dielectric plug positioned at the distal tip of the shell 102. A metallic collar that fits around the dielectric support portion 116 of the coaxial transmission line is soldered to the distal end of the shield in order to form a shield termination 130. The various electrodes and metallic wires are located proximal of the shield termination 130 for protection from the strong electromagnetic fields generated during use. Thus, the shield termination serves as an electromagnetic shield for the electronics. By way of example, the shield termination may be formed of stainless steel for welding attachment or plated with a suitable material for brazing or soldering. In one embodiment, the braided shield may be formed from small, silver-plated copper wires. When such a coaxial transmission line is used, silver solder has been found to work well to couple the shield to the shield termination ring 130.

The steering wire 66 may be formed from any suitable material. By way of example, stainless steel spring wire has been found to work well. The steering wires are attached to the shield termination 130. Since the steering wire 66 will typically be pulled back and forth relatively often during introduction of the catheter into the body of a patient, it is important that the attachment between the steering wire and the shield termination be quite good. A wide variety of soldering, welding, brazing, sintering processes may be used to attach these components. By way of example, a gold weld has been found to work well. Since the overall diameter of the catheter is strictly limited and it is desirable to have the largest diameter coaxial cable that is possible, the steering wires 66 are preferably quite small in diameter. By way of example, steering wires having a diameter of approximately 6–10 mils have been found to work well. When particularly small diameter wires are used, such as steering wires on the order of 4 mils in diameter, it may be desirable to coat the wires in order to prevent the wires from cutting through the tubular member 51 during use. By way of example, Teflon works well as a coating material.

Figure 6:
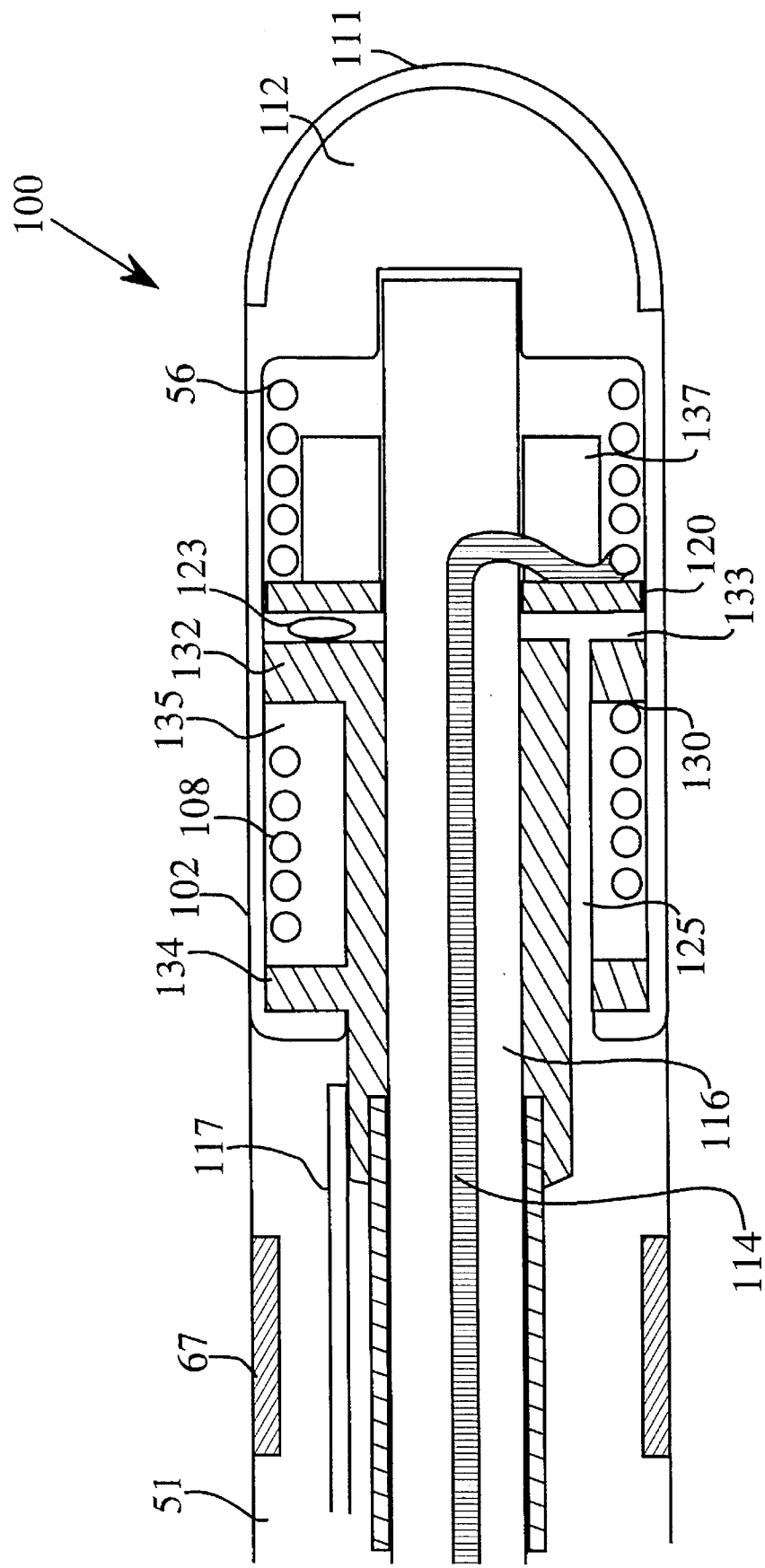
FIG. 6 is a diagrammatic partial cross sectional side view of the end portion of an alternative embodiment of the present invention.

In the described embodiment, the shield termination 130 is simply an annular ring. However, in alternative embodiments, different geometries may be used without departing from the spirit or scope of the invention. By way of example, in embodiments which use a grounding coil, it may be desirable to have an elongated shield termination sleeve having distal and proximal rims which cooperate to form a bobbin-like structure about which the ground coil may be wound as seen in FIG. 6. A wide variety of other shield terminations may be used as well for both anchoring the steering wires and terminating the braided shield. It should be appreciated that the geometry of the shield termination may be varied and configured in a wide variety of manners in order to influence the shape of the electromagnetic field presented by the antenna.

Referring next to FIG. 3, a catheter construction suitable for use with various embodiments of the present invention will be described in somewhat more detail. As seen therein, the tubular member 51 has an elongated central lumen 52, a plurality of stiffener/steering lumens 57, and a plurality of elongated component lumens 59. The central lumen 52 is sized to receive the coaxial transmission line 53. The stiffener/steering lumens 57 receive stiffener wires 58 and steering wires 66, respectively. In the embodiment shown, two opposing stiffening wires 58 are provided and two opposing steering wires 66 are provided. The other various wires (such as the electrode and thermometry wires) may be run through the components lumen 59. Alternatively, in embodiments that utilize one or more inflatable balloons, one of the stiffeners/steering lumens or one of the component lumens 59 may be used to pass a fluid suitable for inflating the balloon(s).

The described tubular members can be fabricated in a wide variety of ways as will be apparent to those skilled in the art. By way of example, medical grade tubing can be drawn in any conventional manner. In a preferred approach, the stiffer tubing and the softer tubing are formed separately and cut to their desired length. The stiffer tubing may make up the bulk of the catheter length (which will of course be dictated by the intended application), while the softer tubing may be closer to two to eight centimeters. By way of example, typical lengths for coronary applications are on the order of 100–130 centimeters. In order to connect the tubing pieces, they may be placed on a jig that preserves the lumen integrity and heated to a temperature just past the glass point. By way of example, when PEBAX tubing is used, bonding temperatures of approximately 300° F are appropriate. With the tubing in such a state, the stiffer and softer tubes may be pressed together to form a thermal bond that, when cooled, is extremely strong.

With the outer tubing 51 fully formed, the electronic wiring that is directly or indirectly coupled to the shield termination may be inserted as a complete assembly. To accomplish this, the antenna 56 is secured to the center conductor of the coaxial transmission line and the shield termination 130 is secured to the shield as described above. Similarly, the steering wires 66 are welded to the shield termination, and the entire assembly may be inserted as a unit into the appropriate lumens in the tubing 51.

Figure 4:
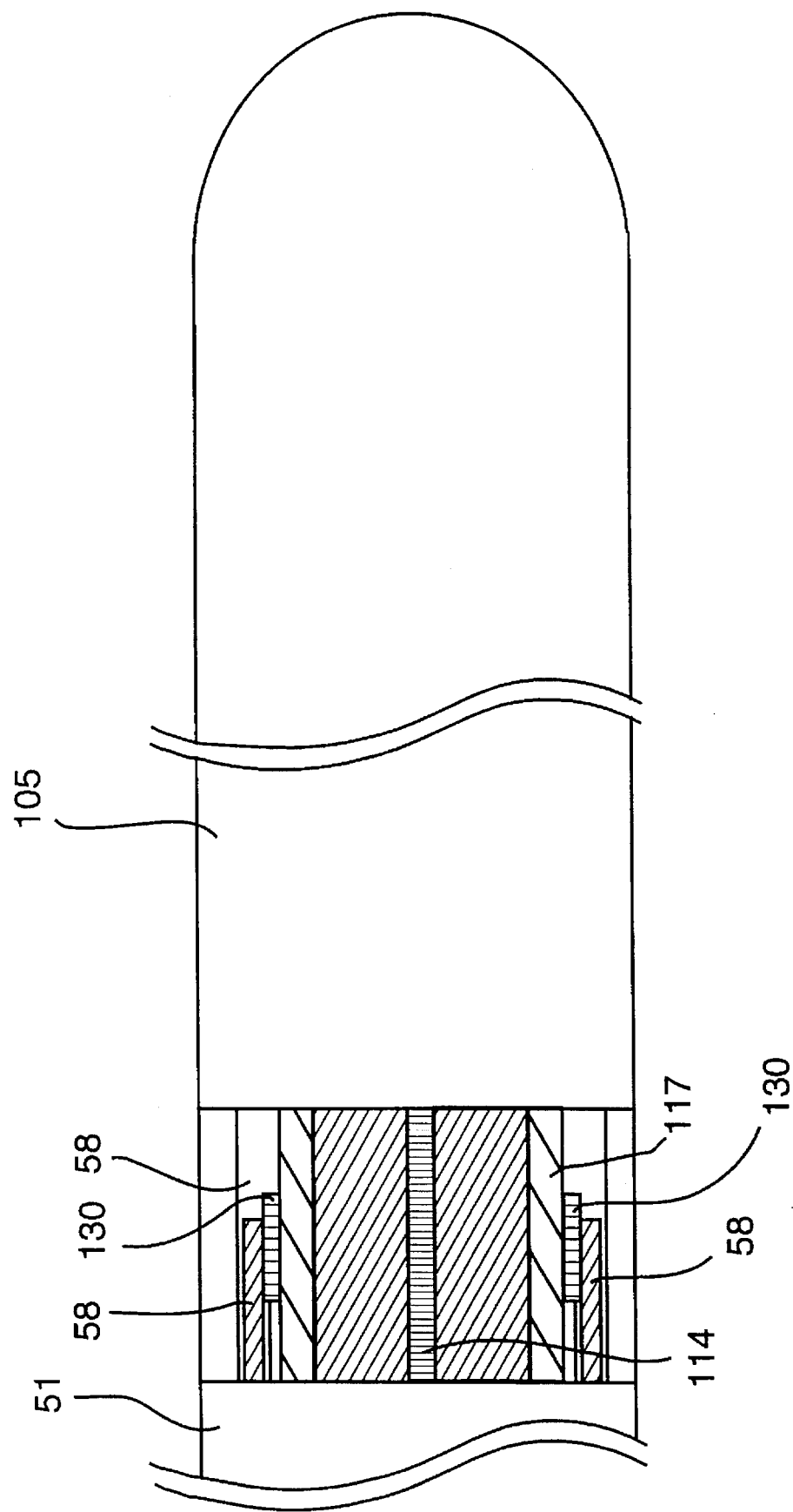
FIG. 4 is a diagrammatic side view illustrating an arrangement for attaching a ring collar to a coaxial transmission line.

In another embodiment, a stiffener collar 180 may be positioned at the junction of the stiff and soft tubings 51,102 as illustrated in FIG. 4. The stiffening collar may then be used to anchor the stiffening wires 58. Like the steering wires, the stiffening wires may be formed from stainless steel spring wire, although frequently they may be slightly larger in diameter if the design permits.

Referring next to FIG. 4, a suitable structure for firmly anchoring the ring collar will be described. In this embodiment, the ring collar 130 has an inner diameter that is similar to the diameter of the tubular member's central lumen 52. The ring collar is positioned to abut against the distal end of the portion of the soft tubular member 105 located between the central lumen 52 and the lumens for the steering wire(s). If desired, an epoxy or other suitable material can be used to further set and secure the collar ring in place.

Figure 5:
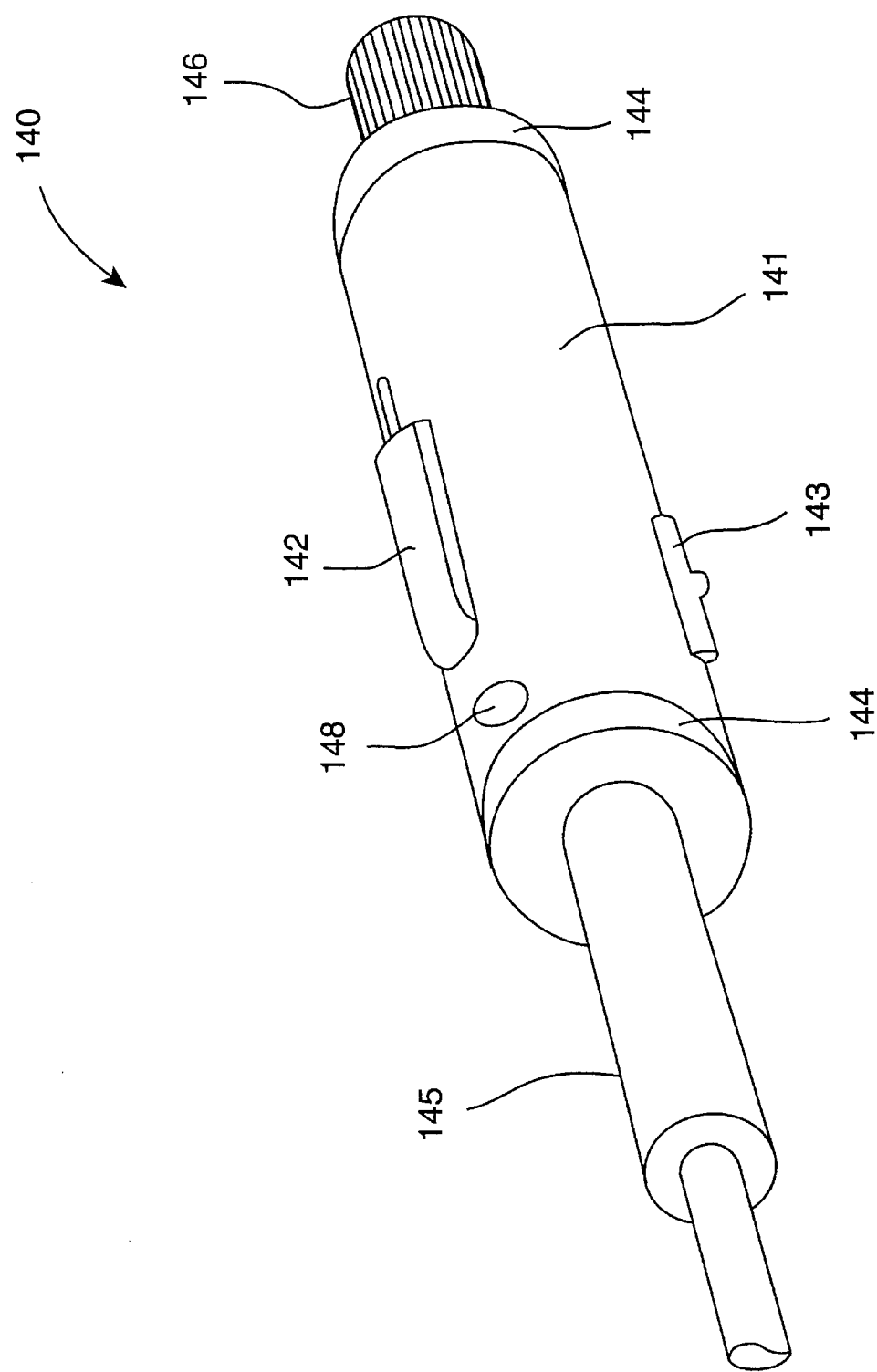
FIG. 5 is a partially broken away diagrammatic illustration of a handle transducer suitable for steering the catheter tip as it is positioned in the body of a patient.

A wide variety of mechanical and electromechanical control mechanisms may be provided to control the actuation of the described steering wires. By way of example, one suitable arrangement for the handle transducer is illustrated in FIG. 5. The handle 140 includes a housing 141, a deflecting slide 142, a locking mechanism 143, housing caps 144, a strain relief 145, and an electrical connector 71. The deflecting slide 142 is coupled to the proximal end of the steering wire, allowing the user to pull on the steering wire via the deflecting slide. Once the catheter is in the desired position, the locking mechanism 143 can be activated to hold the deflecting slide 142 in place. In the embodiment of the handle shown, only one steering wire is used. However, in alternative embodiments, two or more steering wires may be used. A wide variety of mechanisms can be used to facilitate control of the multiple steering wires. By way of example, a spring loaded bobbin may be used to drive dual steering wires by wrapping one wire clockwise and one counterclockwise on the bobbin and coupling one of the wires to the deflecting slide. Of course, a wide variety of structures, both mechanical and electromechanical in nature can be used in place of the described deflecting slide arrangement. An LED 148 may also be provided to show when the ablation catheter is in use. Additionally, the outer surface of the housing 141 may be knurled to facilitate better gripping.

Referring next to FIG. 6, an alternative embodiment of the invention will be briefly described that includes a shield termination 130 having a different geometry. In this embodiment, a tunable antenna is provided as described in the above referenced application. Briefly, shield termination 130 is coupled to the shield portion 117 of the coaxial transmission line 53. The shield termination 130 has an enlarged head 132 at its distal end. The various electrodes and metallic wires are located proximal of the shield termination head for protection from the strong electromagnetic fields generated during use. Thus, the shield termination serves as an electromagnetic shield for the electronics. The catheter tip 100 is encased within an insulating shell 102 formed from a dielectric material such as silicone or Teflon. The shield termination 130 extends proximally beyond the dielectric shell 102 to make a good connection with the shield 117 which anchors the catheter transmission line. The connection can be made using any suitable connection technique such as soldering, brazing or crimping. The shield termination also includes an enlarged anchor portion 134 that mates with the proximal end of the shell to secure the shell in place. The anchor and head portions of the shield termination 130 cooperate to form a bobbin like structure having an opening 135 that receives the ground coil 108. The distal end of the thermometry element 65 (not shown) are positioned behind the head portion 132 of the shield termination. The electrodes 67 are positioned proximally relative to the shell 102. Similarly, the distal end of stiffening/steering wires 58 are also attached to proximal portion of the shield termination by any suitable connection technique such as welding, brazing, soldering or adhesive bonding. The welding technique described above works well. The reason for the positioning of the thermocouple, the electrodes and wire elements behind the shield is to prevent their interference with the electromagnetic field and vice versa.

To adjust the antenna's impedance, a slidable thrust plate 120 is provided between the proximal end of the antenna coil 56 and the shield termination head 132. The thrust plate 120 is driven by a balloon actuator 123 that is located between the thrust plate and the face 133 of the shield termination. Thus, the shield termination 130 acts as a surface against which the balloon actuator 123 may push in order to regulate the position of the thrust plate. The balloon actuator 123 is fed by a feed tube 125. A slider 137 is provided distal of the thrust plate and serves to balance the thrust plate 120 so that it moves evenly in an orientation that is substantially perpendicular to the longitudinal axis of the catheter. More specifically, the slider is secured to the thrust plate and is closely journaled around the dielectric support 116 to insure that the thrust plate 120 does not wobble as it translates. Electrical properties of the slide 137 may be selected appropriately based upon the needs of a particular catheter.

Figure 7:
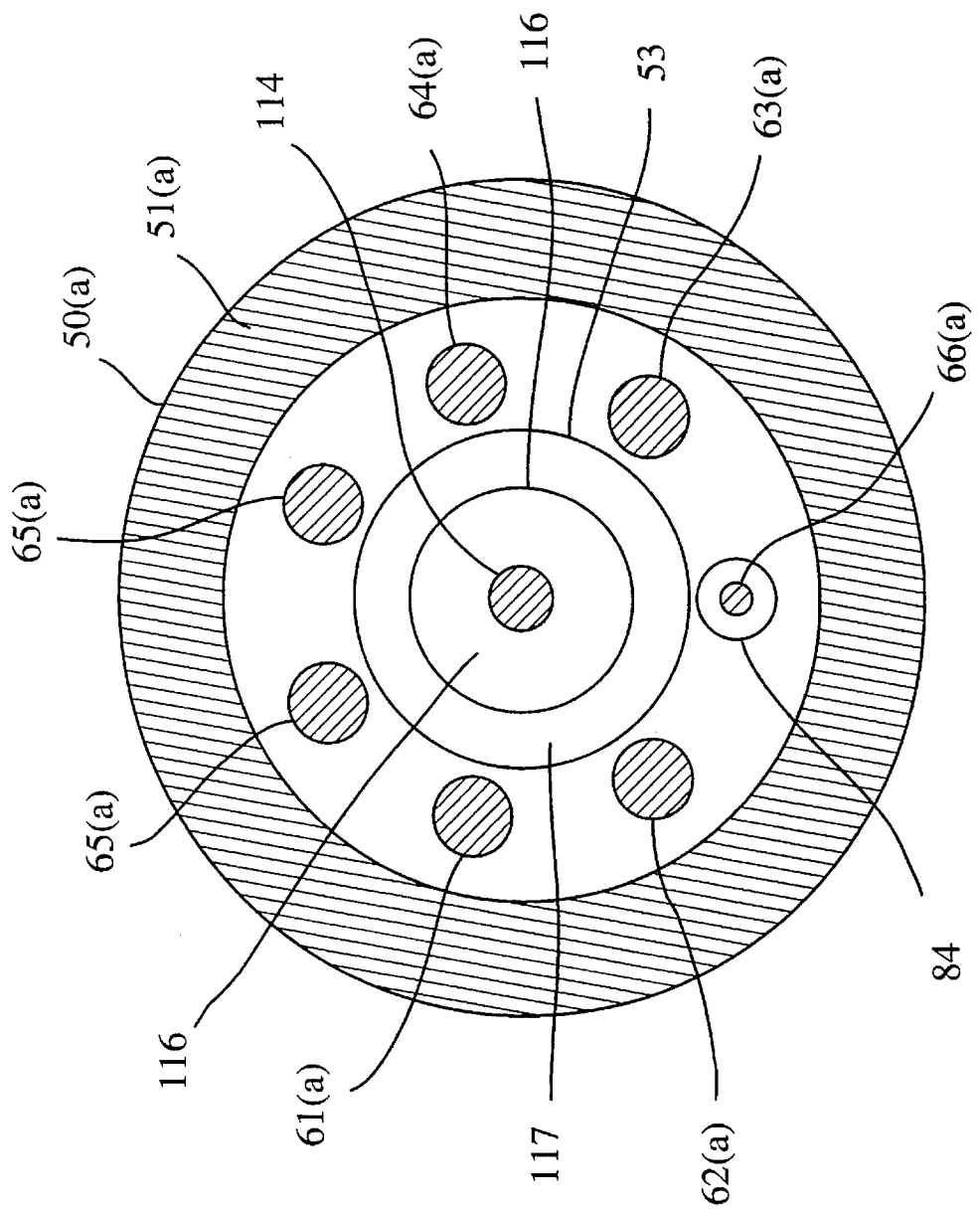

Referring next to FIG. 7, an alternative single lumen catheter construction will be described. In this embodiment, the catheter 50a includes an outer tubing 51a having a single lumen which receives coaxial microwave transmission line 53, a single steering wire 66a which is received with in a steering wire support tube 84, thermometry elements 65a and electrode wires 61a–64a.

Figure 8:
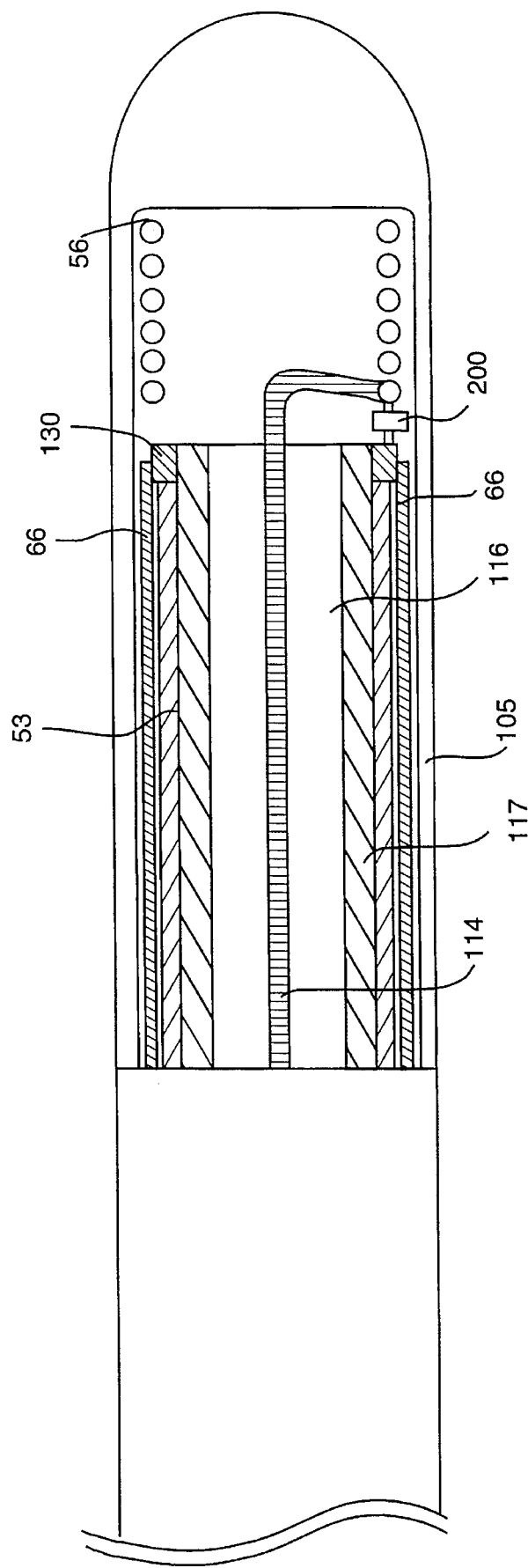
FIG. 8 is a diagrammatic cross sectional side view illustrating the placement of a tuning capacitor used to facilitate impedance matching for the catheter system.

Referring next to FIG. 8, yet another embodiment of the invention will be described. As seen therein, in this embodiment, a tunable capacitor 200 is also provided to electrically facilitate the adjustment of the antenna's impedance. By way of example, the tunable capacitor may take the form of a Veractor diode. In the embodiment shown, the Veractor diode is coupled between the antenna 56 and the shield termination 130. Tuning may be accomplished by applying s D.C. tuning voltage to the center conductor. It should be appreciated that the applications referenced above disclose a number of methods of tuning the catheter system in order to facilitate impedance matching. The method described herein which incorporates a tunable capacitor may be used either standing alone or in conjunction with other tuning systems such as those described in the above referenced applications.

Figure 9:
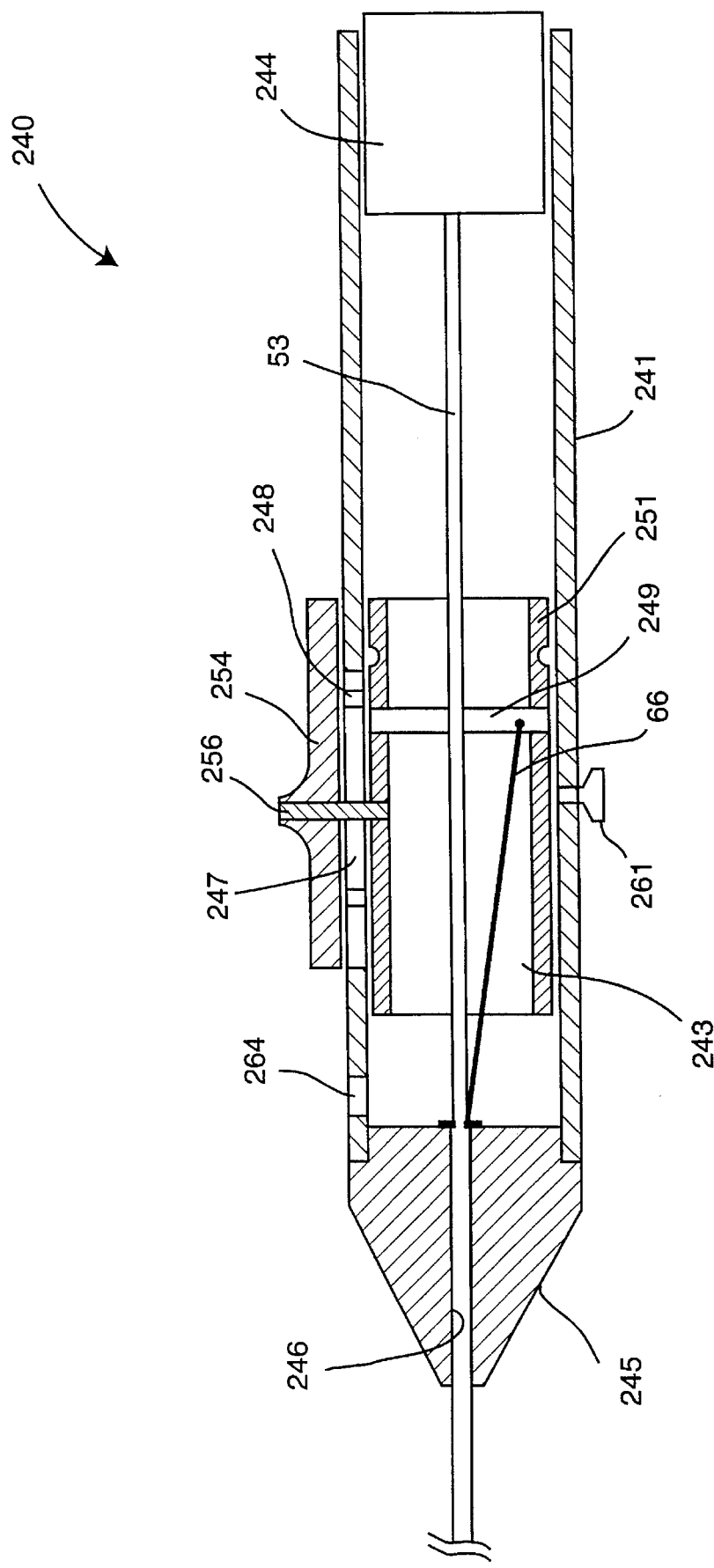
FIG. 9 is a diagrammatic side view of an alternative handle transducer embodiment suitable for steering the catheter tip as it is positioned in the body of a patient.

Referring next to FIG. 9, another embodiment of a handle suitable for actuating a single steering wire will be described. In this embodiment, the handle 240 includes a tubular housing 241, a slider 243 that is slidable relative to the housing, an electrical connector 244 that plugs the proximal end of the housing and a distal cap 245. The catheter 50 is received into the handle through a concentric bore 246 in the distal cap 245. The distal cap is then used to anchor the catheter's outer tubing 51. The slider 243 is used to anchor steering wire 66 and thus movements of the slider relative to the housing effectively pull or push the steering wire causing corresponding deflections of the catheter tip as described above. The electrical components including the transmission line 53 pass through the tubular housing to the electrical connector 244. The connector 244 is preferably adapted for connection to wiring from a power supply.

The housing 241 is substantially tubular in shape and has a longitudinally extending slot 247 on one surface. The slider 243 includes a substantially tubular guide 251 that is slidably received within the housing 24 1, a thumb knob 254 that is positioned external to the housing and a connecting post 256 that extends through the slot 247 to couples the thumb knob and the slider together. A pair of pegs 248 are also coupled to the thumb knob 254 such that they extend into the slot 247. The pegs are positioned longitudinally on opposite sides of post 256 and cooperate with the proximal and distal ends of the slot 247 to limit the movement of the thumb knob. An anchor ring 249 is provided on the slider and serves as an anchor point for the steering wire. That is, the steering wire is attached to the anchor ring. With this construction, the thumb knob may be used to push and pull the steering wire back and forth and the pegs 248 effectively limit the movement of the steering wires.

A locking thumb screw 261 may also be provided that extends through and is threadably engaged with one wall of the housing such that it can contact the guide 251. The thumb screw 261 may be used by the operator to lock the slider (and thus the steering wire) in place. Additionally, an LED 264 is mounted on the surface of the housing 241 such that it is readily visible by the operator. As described above, the LED may be used to indicate when the ablation catheter is in use. That is, when the power is on.

Although only a few embodiments of the present invention have been described in detail, it should be understood that the present invention may be embodied in many other specific forms without departing from the spirit or scope of the invention. Particularly, the invention has been described in terms of a microwave ablation catheter for cardiac applications. However, it should be appreciated that the described small diameter microwave ablation catheter could be used for a wide variety of alternative applications as well. Further, although the coaxial transmission line described works extremely well for microwave applications, it may be used to transmit electromagnetic energy at other frequencies as well, and accordingly the described invention may be used in conjunction with a wide variety of catheters. Further, the described ring structure in conjunction with the softened end portion of the catheter can be applied to various other catheters such as mechanical atherectomy devices and other catheters that utilize mechanical transmission lines to modulate a working component. One advantage of the ring structure is that it permits the transmission line to pass the center thereof.

Although a specific antenna geometry has been described, it should be appreciated that the invention is quite independent of the antenna geometry and may be used in conjunction with a variety of different ablation catheters. Similarly, as should be apparent from the two described tip constructions, a wide variety of antenna constructions may be used in accordance with the described invention. Further, although a specific handle transducer has been described, it should be appreciated that a wide variety of alternative mechanisms could be provided to actuate the steering wires. Accordingly, the catheter design, the power supply design, the actuator design and the shield termination design may all be modified within the scope of this invention. Therefore, the present examples are to be considered as illustrative and not restrictive, and the invention is not to be limited to the details given herein, but may be modified within the scope of the appended claims.

We claim:

1. A medical catheter comprising:

a flexible tubular member having a distal end, the tubular member being adapted to be inserted into a vessel in the body of a patient, a first portion of the tubular member having a stiffness that is significantly less than the stiffness of the majority of the tubular member, the first portion of the tubular member being located near the distal end of the tubular member, an anchor ring secured to said tubular member near the distal end, of the tubular member, the anchor ring being located near the first portion of the tubular member, the anchor ring near the distal end of the catheter being formed from a material that is electrically conductive;

a working member disposed distally of the anchor ring;

an elongated transmission line received within the flexible tubular member for transmitting energy to the working member, the transmission line being electrically coupled to the anchor ring and arranged to pass through said anchor ring; and at least one steering wire that extends through said tubular member and is anchored to the anchor ring;

whereby when the catheter is inserted into the vessel of a patient, the distal end of the catheter may be steered by pulling on the steering wire.

2. A medical catheter as recited in claim 1 wherein a pair of steering wires are provided with each steering wire being anchored to the anchor ring.

3. A medical catheter as recited in claim 1 wherein the flexible tubular member includes a plurality of lumens and the steering wire is disposed within a first lumen and the transmission line is disposed within a second lumen.

4. A medical catheter as recited in claim 1 wherein:

the transmission line is an elongated coaxial transmission line that includes a center wire, a shield and a dielectric that electrically insulates the center wire from the shield;

the working member is an antenna carried at the distal end of the coaxial transmission line; and wherein the anchor ring further acts as an electrical conduit between the shield of the coaxial transmission line and an electromagnetic field emanating from the antenna.

5. A medical catheter as recited in claim 4 wherein the catheter is a microwave ablation catheter.

6. A medical catheter as recited in claim 1 further comprising a handle for permitting an operator to control movements of the catheter, the handle being located near a proximal end of the outer tubing, the handle including:

a housing that is sized to be readily grasped by an operator;

a slider that is slidable relative to the housing, the slider serving as an anchor for a proximal end of the steering wire and including a knob that an operator may actuate to push and pull the steering wire, the knob being attached to the slider.

7. A medical catheter as recited in claim 6, wherein:

the housing includes a slot;

the slider further includes, a tubular guide received within the housing for movement back and forth within the housing, the tubular guide being arranged to receive the transmission line there through, a connecting post that extends through the slot to the knob for coupling the knob to the tubular guide, and a peg that extends into the slot, the peg being arranged to limit the movement of the slider; and the handle further includes an anchor ring mounted on the tubular guide, the steering wire being attached directly to the anchor ring to anchor the steering wire to the slider.

8. A medical catheter comprising:

a flexible tubular member having a lumen therein, the tubular member being adapted to be inserted into a vessel in the body of a patient;

an elongated coaxial transmission line received within a lumen in the flexible tubular member, the coaxial transmission line including a center conductor, a shield and a dielectric that electrically insulates the center conductor from the shield, the shield having a distal end;

an antenna carried by the coaxial transmission line;

an electrically conductive shield termination attached to the distal end of the shield portion of the coaxial transmission line, the shield termination being arranged proximally of the antenna; and a steering wire that extends through the tubular member and is attached to the shield termination;

whereby when the catheter is inserted into the vessel of a patient, the tip of the catheter may be steered by pulling on the steering wire.

9. A medical catheter as recited in claim 8 wherein a pair of steering wires are provided with each steering wire being anchored to the shield termination.

10. A medical catheter as recited in claim 8 wherein the shield termination is annular in nature and includes a central opening, and wherein the center conductor and dielectric portions of the coaxial transmission line pass through the central opening of the shield termination.

11. A medical catheter as recited in claim 8 wherein:

the flexible tubular member has a plurality of lumens, the coaxial transmission line being received within a first lumen and the steering wire being received within a second lumen; and the shield termination is arranged to abut against a structural portion of the tubular member disposed between the first and second lumens.

12. A method of forming a microwave ablation catheter having a coaxial transmission line having a center conductor portion having a distal end, a braided shield portion having a distal end, and an antenna electrically coupled to the distal end of said center conductor portion of the coaxial transmission line, the method comprising the steps of:

forming an elongated flexible tubular member having a tubular end that is sized suitably to be inserted into a vessel in the body of a patient, such that a first portion of the tubular member has a stiffness that is significantly less than the stiffness of the majority of the tubular member, the first portion of the tubular member being located near the distal end of the tubular member;

securing an electrically conductive shield termination ring to the distal end of a braided shield portion of the coaxial transmission line;

attaching steering wires to the shield termination ring; and inserting the coaxial transmission line and the steering wires into the flexible tubular member; and forming a cap over the antenna, the cap being sealed to the flexible tubular member.

13. A method as recited in claim 12 wherein the shield termination is welded to the braided shield.

14. A method as recited in claim 12 wherein the steering wires are welded to the shield termination.

15. A method as recited in claim 12 wherein the antenna is attached to a center conductor of the coaxial transmission line, the shield termination is attached to the shield portion of the coaxial transmission line, and the steering wires are attached to the shield termination prior to their insertion into the tubular member.

16. A method as recited in claim 12 wherein the tubular member forming step includes the substeps of:

forming the first portion of the tubular member from a material having a first stiffness;

forming a second portion of the tubular member from a material having a second stiffness, the second portion of the tubular member being stiffer than the first portion of the tubular member and constituting the majority of the tubular member; and heating the first and second portions of the tubular member to a glass point and bonding the first and second portions of the tubular member together at their glass point.

* * * * *